United States Patent [19]

Chouraqui

[11] Patent Number: 5,510,108
[45] Date of Patent: Apr. 23, 1996

[54] SANITIZER FOR SWIMMING POOLS, SPAS, AND HOT TUBS

[75] Inventor: Richard J. Chouraqui, Paris, France

[73] Assignee: Olin Corporation, Cheshire, Conn.

[21] Appl. No.: 383,478

[22] Filed: Feb. 1, 1995

[51] Int. Cl.$^6$ .............. A01N 25/34; A61K 9/26; C02F 1/76; C02F 1/68
[52] U.S. Cl. .............. 424/408; 424/405; 424/464; 424/469; 424/470; 210/755; 210/764
[58] Field of Search .................. 424/464, 469, 424/470, 489, 405, 408; 210/755, 764

[56] References Cited

U.S. PATENT DOCUMENTS

| | | | |
|---|---|---|---|
| 4,054,518 | 10/1977 | Gould | 210/61 |
| 4,472,187 | 9/1984 | Wojtowicz | 504/155 |
| 4,498,921 | 2/1985 | Wojtowicz | 504/151 |
| 4,952,398 | 8/1990 | Tapin | 71/67 |
| 5,106,559 | 4/1992 | Wiedrich et al. | 264/122 |

*Primary Examiner*—Carlos Azpuru
*Attorney, Agent, or Firm*—William A. Simons

[57] ABSTRACT

A sanitizer composition comprising a bactericidal effective amount of the combination of (a) chlorinated isocyanuric acids such as trichloroisocyanuric acid or sodium dichloroisocyanurate and alkali metal salts thereof; (b) aluminum sulfate; and (c) copper sulfate.

13 Claims, No Drawings

SANITIZER FOR SWIMMING POOLS, SPAS, AND HOT TUBS

BACKGROUND OF THE INVENTION

1. Field of the Invention

This invention relates to selected sanitizer compositions comprising a combination of chlorinated isocyanuric acids or salts thereof, aluminum sulfate, and copper sulfate.

2. Brief Description of Prior Art

Water in swimming pools, spas, and hot tubs is constantly recirculated and fresh water is normally added only to maintain the desired volume. Although this water is usually filtered continuously to keep it free of suspended matter, it frequently contains bacteria. Treatment with one or more sanitizers to control the bacteria count is necessary.

Numerous chemical compounds have been used in swimming pools, spas, and hot tubs. Chlorinated isocyanuric acids, such as trichloroisocyanuric acid (TCCA), or dichloroisocyanuric acid (DCCA) and their salts such as sodium dichloroisocyanurate (SDCC) have been used. See U.S. Pat. Nos. 4,472,187 and 4,498,921, both of which issued with John Wojtowicz as the named inventor.

Copper sulfate has been used as an algicide in conjunction with TCCA. See column 3, lines 45–63 of the Wojtowicz '187 patent.

There is still a need in the art for better performing pool sanitizers. The present invention provides a solution to that need.

BRIEF SUMMARY OF THE INVENTION

Accordingly, the present invention is directed to a sanitizer composition comprising a bactericidal effective amount of the combination of (a) chlorinated isocyanuric acids or alkali metal salts thereof; (b) aluminum sulfate; and (c) copper sulfate.

DESCRIPTION OF PREFERRED EMBODIMENTS

The present application recites "a bactericidal effective amount of the combination" of the above-noted three critical ingredients. This term, as used in the present specification and claims, means that any total amount of these three components that results in an effective bactericidal activity against at least 99.9%, preferably 99.99%, of the bacteria initially present in the water treated with said combination. In other words, if a body of water containing one million colony forming units (CFUs) of bacteria per milliliter was treated in accordance with the present invention, then less than 1,000 colony forming units (CFUs), or preferably less than 100 CFUs, will be left per milliliter after contact with this combination.

Preferred chlorinated isocyanuric acids and salts thereof include dichloroisocyanuric acid (DCCA), trichloroisocyanuric acid (TCCA), or alkali metal salts thereof such as sodium dichloroisocyanurate (SDCC) in either granular or powdered form or combinations thereof. Any reference to such salts herein, whether specific or in general, refers to both the anhydrous form as well as any hydrates thereof. The most preferred sanitizers are either trichloroisocyanuric acid or sodium dichloroisocyanurate. Granular TCCA or SDCC generally has an average particle size from about 200 to about 2,000 microns. Powdered TCCA or SDCC generally has a particle size from about 40 to about 200 microns. The combination of granular TCCA and powdered TCCA are especially preferred wherein the ratio by weight of granular TCCA to powdered TCCA is from about 5:1 to about 1:1, preferably from about 3:1 to about 1.5:1.

The aluminum sulfate (which may be either the anhydrous form or its hydrates) is preferably used in powdered form where the average particle size is from about 50 to about 3,000 microns.

The copper sulfate ($CuSO_4$) (both its anhydrous and hydrate forms) is preferably used in powdered form (sometimes also called "snow") where the average particle size is from about 100 to about 1,000 microns. The pentahydrate powder is the most preferred form.

Optionally, boric acid may be added to the above mixture. The preferred form of the boric acid is a powdered form where the average particle size is from about 10 to about 200 microns.

Those ingredients are combined in the following percentage by weight ranges:

| Ingredient | Preferred | More Preferred |
|---|---|---|
| Trichloroisocyanuric Acid or Sodium Dichloroisocyanurate | 80–95% | 82–92% |
| Aluminum Sulfate | 5–15% | 7–13% |
| Copper Sulfate | 0.1–1.5% | 0.2–1.0% |
| Boric Acid | 0–3% | 0–1.5% |

These ingredients may be combined in any suitable way. One preferred method is a V-Blender apparatus.

After the ingredients have been combined together, the combination is preferably formed into suitable-sized tablet. Any conventional pool sanitizer tableting equipment that is useful for making TCCA or SDCC tablets may be useful in this invention. Alternatively, bags of the loose granular and powdered ingredients within the above percentage ranges may be prepared for use.

The chemical combinations of the present invention may be added to pools, spas, or hot tubs in either tablet or loose granular/powdered form. Generally, a sufficient amount of the combination of the present invention should be added often enough to be an effective bactericidal amount initially and to maintain that bactericidal effect in the pool, spa, or hot tub. Preferably, a 500 gram tablet of the combination is sufficient to sanitize about 30,000 liters of swimming pool water for 7 days.

The following experiment is provided to better understand the present invention. All parts and percentages are by weight and all temperatures are degrees Celsius, unless explicitly stated otherwise.

EXAMPLE 1

Slow dissolving tablets, weight 500 grams, having a 90 mm diameter, and having 81% available chlorine were prepared by mixing and tableting the following ingredients in the following percentages:

| | |
|---|---|
| Granular trichloroisocyanuric acid | 56.6% |
| Powdered trichloroisocyanuric acid | 32.4 |
| Powdered aluminum sulfate | 9.4 |
| Powdered boric acid | 1.0 |

| | |
|---|---|
| Copper sulfate pentahydrate snow | 0.7 |
| Total | 100.1% |

These ingredients were mixed in a V-Blender and tableted with a hydraulic press using a pressure of kg/cm$^2$.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A sanitizer composition comprising a bactericidal effective amount of the combination of (a) chlorinated isocyanuric acid and alkali metal salts thereof; (b) aluminum sulfate; and (c) copper sulfate; and wherein the percentage ranges by weight of each ingredient are as follows:

| | |
|---|---|
| Chlorinated isocyanuric acid and alkali metal salts thereof | 80–95% |
| Aluminum Sulfate | 5–15% |
| Copper Sulfate | 0.1–1.5%. |

2. The sanitizer composition of claim 1 wherein said sanitizer composition additional comprises boric acid in a percentage range by weight of up to 3%.

3. The sanitizer composition of claim 1 wherein said aluminum sulfate is present in the form of powdered particles having an average particle size from about 50 microns to about 3,000 microns.

4. The sanitizer composition of claim 1 wherein said copper sulfate is present in the form of powdered particles having an average particle size from about 100 microns to about 1,000 microns.

5. The sanitizer composition of claim 1 wherein said chlorinated isocyanuric acid and alkali metal salts thereof is trichloroisocyanuric acid.

6. The sanitizer composition of claim 5 wherein said sanitizer composition optionally contains boric acid and the percentage ranges by weight of each ingredient are as follows:

| | |
|---|---|
| Trichloroisocyanuric acid | 82–92% |
| Aluminum sulfate | 7–13% |
| Copper sulfate | 0.2–1.0% |
| Boric acid | 0–1.5% |

7. The sanitizer composition of claim 5 wherein a mixture of granular and powdered trichloroisocyanuric acid is employed in a ratio from about 5:1 to about 1:1 by weight granular particles to powdered particles.

8. The sanitizer composition of claim 7 wherein said granular particles of trichloroisocyanuric acid have an average particle size from about 200 to about 2,000 microns.

9. The sanitizer composition of claim 7 wherein said powdered particles of trichloroisocyanuric acid have an average particle size from about 40 microns to about 200 microns.

10. The sanitizer composition of claim 5 wherein said sanitizer composition additionally comprises boric acid in a percentage range of up to 3%.

11. The sanitizer composition of claim 1 wherein said chlorinated isocyanuric acid and alkali metal salt thereof is sodium dichloroisocyanurate.

12. The sanitizer composition of claim 11 wherein said sanitizer composition optionally contains boric acid and the percentage ranges by weight of each ingredient are as follows:

| | |
|---|---|
| Sodium Dichloroisocyanurate | 82–92% |
| Aluminum sulfate | 7–13.% |
| Copper sulfate | 0.2–1.0% |
| Boric acid | 0–1.5% |

13. The sanitizer composition of claim 11 wherein said sanitizer composition additionally comprises boric acid in a percentage range of up to 3%.

* * * * *